(12) United States Patent
Yoshida et al.

(10) Patent No.: US 11,344,274 B2
(45) Date of Patent: May 31, 2022

(54) RADIOGRAPHIC IMAGING APPARATUS

(71) Applicant: Shimadzu Corporation, Kyoto (JP)

(72) Inventors: Koki Yoshida, Kyoto (JP); Yoshihide Magari, Kyoto (JP); Fumiaki Tanaka, Kyoto (JP); Takanori Yoshida, Kyoto (JP); Shinya Hasebe, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 15 days.

(21) Appl. No.: 17/156,594

(22) Filed: Jan. 24, 2021

(65) Prior Publication Data
US 2021/0228174 A1 Jul. 29, 2021

(30) Foreign Application Priority Data

Jan. 28, 2020 (JP) .............................. JP2020-011489

(51) Int. Cl.
*H01J 37/20* (2006.01)
*A61B 6/00* (2006.01)
*G06F 3/04812* (2022.01)
*G06F 3/04847* (2022.01)

(52) U.S. Cl.
CPC ................ *A61B 6/54* (2013.01); *A61B 6/463* (2013.01); *A61B 6/465* (2013.01); *G06F 3/04812* (2013.01); *G06F 3/04847* (2013.01)

(58) Field of Classification Search
CPC ........... A61B 6/54; A61B 6/465; A61B 6/463; G06F 3/04812; G06F 3/04847; G06F 3/048; G06F 3/00; G06F 3/04815; G06F 3/0488; H04N 1/00411; H01J 37/20
See application file for complete search history.

(56) References Cited

U.S. PATENT DOCUMENTS

2018/0337018 A1 11/2018 Adachi

FOREIGN PATENT DOCUMENTS

| CN | 103764030 A | * | 4/2014 | ........... A61B 6/4452 |
|---|---|---|---|---|
| JP | 2018191976 A | | 12/2018 | |

* cited by examiner

*Primary Examiner* — Don K Wong
(74) *Attorney, Agent, or Firm* — Muir Patent Law, PLLC (57) ABSTRACT

Provided is a radiographic imaging apparatus capable of easily and properly performing a selection operation or a playback operation of the moving image and a frame feeding operation of the moving image. An operation unit is provided with a tiltable lever and a rotation input portion provided at an upper end of the lever. The image processing unit performs a selection operation or a playback operation of the moving image to be displayed on the display unit according to a tilting operation of the lever, and performs a frame feeding operation of the moving image to be displayed on the display unit according to a rotating operation of the rotation input portion.

4 Claims, 8 Drawing Sheets

RADIOGRAPHIC IMAGING APPARATUS

CROSS-REFERENCE TO RELATED APPLICATIONS

This application claims priority under 35 U.S.C. § 119 to Japanese Patent Application No. 2020-011489 filed on Jan. 28, 2020, the entire disclosure of which is incorporated herein by reference in its entirety.

BACKGROUND OF THE INVENTION

Field of the Invention

This invention relates to a radiographic imaging apparatus.

Description of the Related Art

An X-ray imaging apparatus as a radiographic imaging apparatus is provided with a top board movable in a state in which a subject is placed thereon, an X-ray irradiation unit for irradiating a subject placed on the top board with X-rays, an X-ray detection unit for acquiring an X-ray image by detecting X-rays emitted from the X-ray irradiation unit and passed through the subject, and a display unit for displaying the X-ray image acquired by the X-ray detection unit. The X-ray irradiation unit and the X-ray detection unit are integrally supported by, for example, a C-shaped arm in a movable manner so that X-ray continuous imaging can be performed on a subject from various directions at a predetermined frame rate.

Such an X-ray imaging apparatus is provided with a moving operation unit for performing an operation for horizontally moving or tilting the top board and further performing an operation for moving the C-shaped arm, and an operation unit for a moving image configured to perform various operations on the moving image obtained by a continuous X-ray imaging to be displayed on the display unit. The operation unit for a moving image is provided with a tiltable lever. By tilting the lever, the selection operation or the playback operation of the moving image and the frame feeding operation of the moving image are performed (see Patent Document 1).

PRIOR ART DOCUMENT

Patent Document

Patent Document 1: Japanese Unexamined Patent Application Publication No. 2018-191976

SUMMARY OF THE INVENTION

Problems to be Solved by the Invention

When the tiltable lever as described in Patent Document 1 is operated to perform the selection operation or the playback operation of the moving image and the frame feeding operation of the moving image, the lever needs to be finely tilted in order to perform the frame feeding operation of the moving image. On the other hand, when performing an surgery or the like on a subject, it is difficult to finely operate the lever because the operation unit is covered with a sterilization cover, and even if it is intended to perform the frame feeding only by one frame, a plurality of frame feeds may be unintentionally performed in some cases. Also, the sterilization cover may cause the lever to tilt in an unintentional direction of the operator.

For example, in a case where an intravascular treatment of a subject is performed, in order to carry an intravascular device, such as, e.g., a catheter, to a treatment site, it is required to quickly display the optimum reference image frame, such as, e.g., one frame having the highest filling degree of a contrast agent. Therefore, when an unintended frame feeding occurs, there is a problem that the treatment is obstructed.

The present invention has been made in order to solve the above-described problems, and an object of the present invention is to provide a radiographic imaging apparatus capable of easily and properly performing a selection operation or a playback operation of a moving image and a frame feeding operation of the moving image.

Means for Solving the Problem

According to one aspect of the present invention, a radiographic imaging apparatus includes:

an imaging system configured to perform continuous imaging at a predetermined frame rate by detecting radiation by a radiation detection unit, the radiation being emitted from a radiation irradiation unit and passed through a subject;

a storage unit configured to store a plurality of radiographic images continuously captured by the imaging system as a moving image;

a display unit;

an operation unit configured to perform an operation of a display of the moving image for the display unit, the moving image being stored in the storage unit; and an image processing unit configured to cause the display unit to display the moving image stored in the storage unit according to an operation of the operation unit, wherein the operation unit includes a tiltable lever and a rotation input portion provided at an upper end of the lever, and wherein the image processing unit performs a selection or a playback of the moving image to be displayed on the display unit according to a tilting operation of the lever, and performs a frame feeding operation of the moving image to be displayed on the display unit according to a rotating operation of the rotation input portion.

Effects of the Invention

According to the first aspect of the present invention, the operation of the lever and the operation of the rotation input portion make it possible to easily and properly perform the selection operation or the playback operation of the moving image and the frame feeding operation.

EMBODIMENTS FOR CARRYING OUT THE INVENTION

Figure 1:
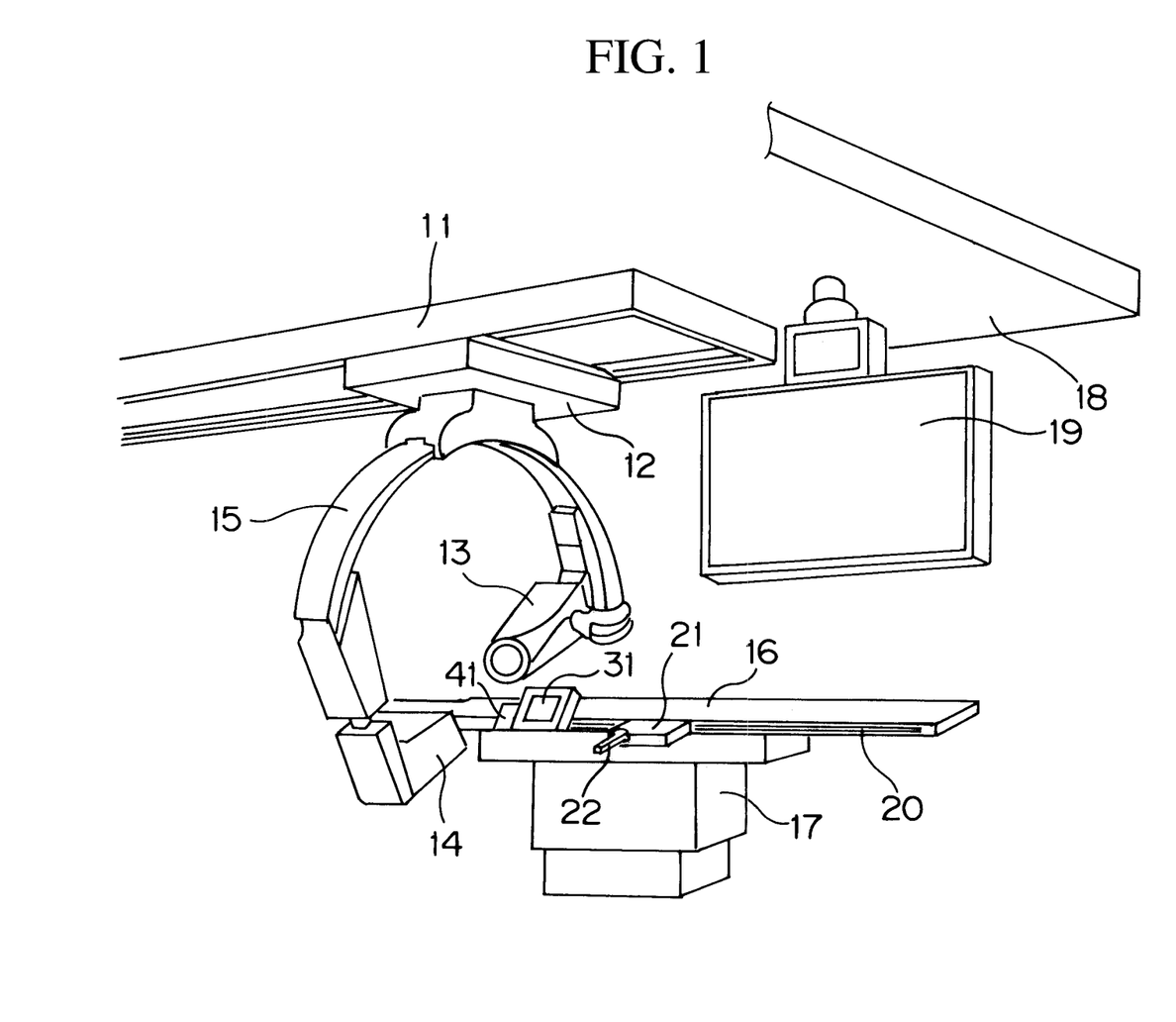
FIG. 1 is a perspective view of an X-ray imaging apparatus.

Hereinafter, some embodiments of the present invention will be described with reference to the attached drawings. FIG. 1 is a perspective view of an X-ray imaging apparatus as a radiographic imaging apparatus according to an embodiment of the present invention.

The X-ray imaging apparatus is for performing continuous imaging for continuously performing X-ray imaging at a predetermined frame rate. The X-ray imaging apparatus is provided with an imaging system including an X-ray irradiation unit 13 for irradiating a subject on a top board 16 supported by a support portion 17 with X-rays and an X-ray detection unit 14 having an X-ray detector, such as, e.g., an FPD (flat panel detector) and an LI (Image Intensifier) for detecting X-rays that have passed through the subject. The X-ray irradiation unit 13 and the X-ray detection unit 14 are supported by a C-shaped arm 15 substantially formed in a C-shape. This C-shaped arm 15 is supported by a carriage 12 which moves in one direction by being guided by a guide member 11 fixed to a ceiling 18.

Further, this X-ray imaging apparatus is provided with a display unit 19 for displaying an X-ray image acquired by the X-ray detection unit 14. This display unit 19 is suspended from the ceiling 18. Note that although FIG. 1 shows that the display unit 19 is composed of a single monitor, the display unit 19 may be composed of a plurality of monitors.

A rail 20 is provided on a side surface of the top board 16. Attached to the rail 20 are a moving operation unit 21 having a lever 22 for horizontally moving or tilting the top board 16 and moving the C-shaped arm 15, a first operation unit 31 provided with a touch panel 32 (see FIG. 2) having a display function and an input function, and a second operation unit 41 which is an operation unit for a moving image for performing various operations on a moving image to be displayed on the display unit 19, the moving image being acquired by continuous X-ray imaging.

Figure 2:
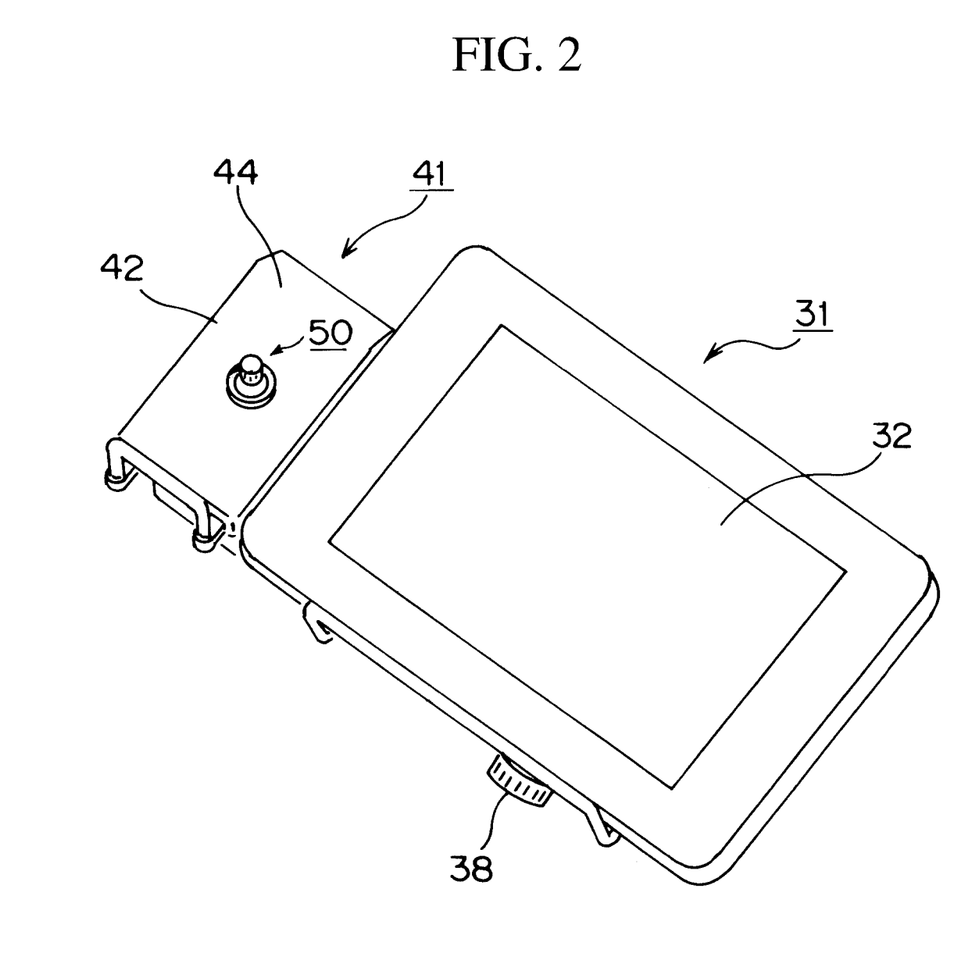
FIG. 2 is a perspective view of a first operation unit 31 and a second operation unit 41.
Figure 3:
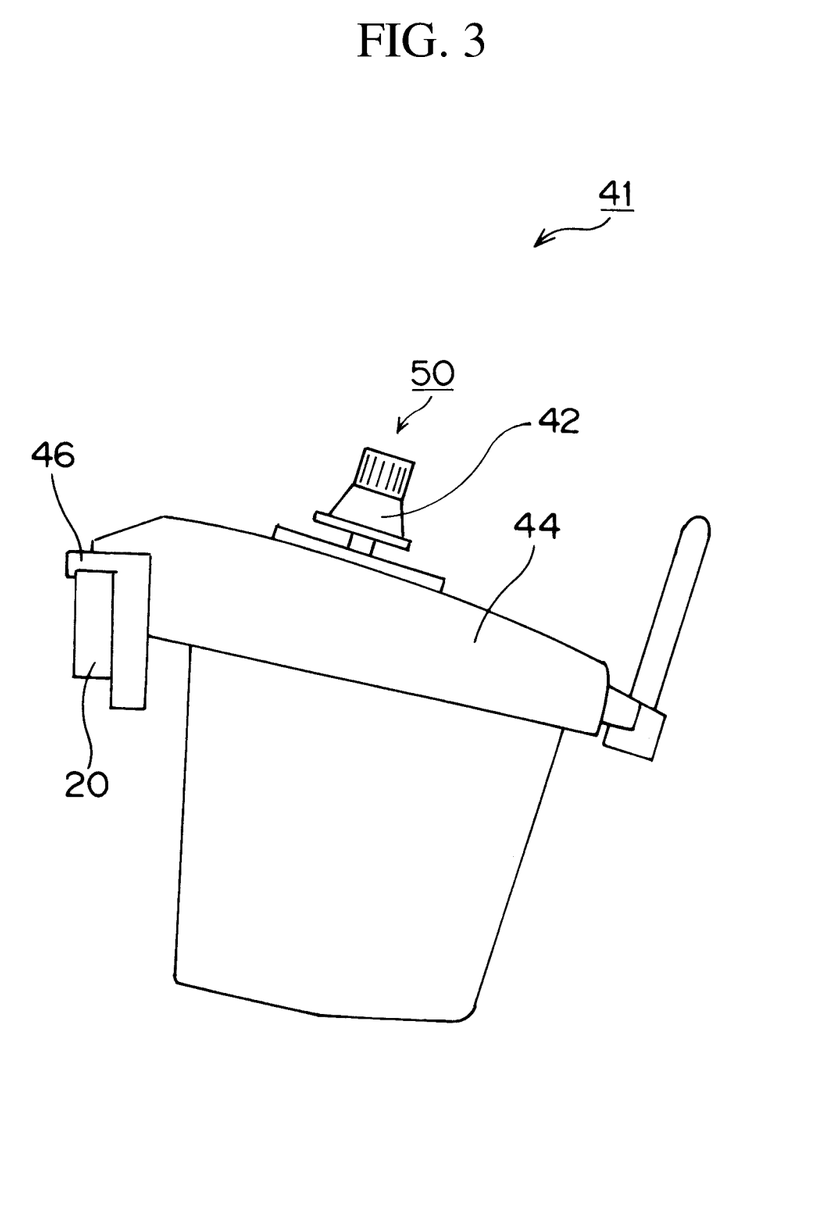
FIG. 3 is a side view showing a state in which a second operation unit 41 is mounted on a rail 20.

FIG. 2 is a perspective view of the first operation unit 31 and the second operation unit 41. FIG. 3 is a side view showing a state in which the second operation unit 41 is mounted on the rail 20.

This first operation unit 31 is provided with a touch panel 32 having an input function and a display function for performing inputs for various operations. The first operation unit 31 is fixed to the rail 20 shown in FIG. 1 by the action of the screw 38 and is mounted on the lateral side of the top board 16. The mounting angle of the first operation unit 31 can be adjusted by the operating of the operator. The second operation unit 41 is provided with an operation unit 50 for operating the display of the moving image to the display unit 19. The second operation unit 41 is mounted to the side of the top board 16 by engaging the mounting portion 46 with the rail 20.

Figure 4:
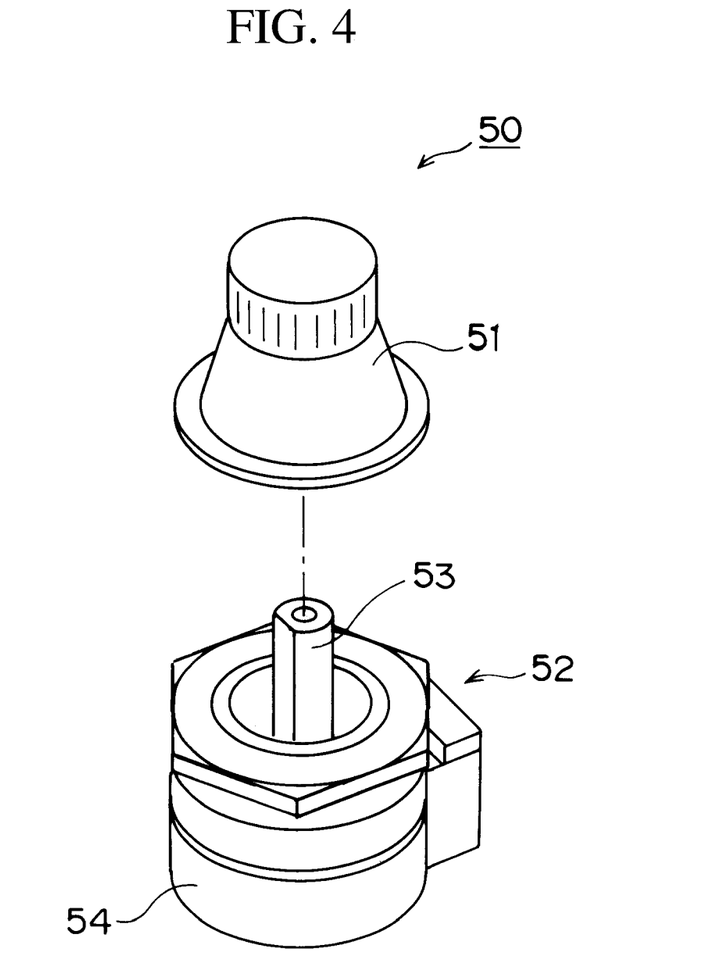
FIG. 4 is an exploded perspective view of an operation unit 50 in a second operation unit 41.

FIG. 4 is an exploded perspective view of the operation unit 50 in the second operation unit 41.

This operation unit 50 is for operating the display of a moving image to be displayed on the display unit 19 and is composed of a rotation input portion 51 for an operator to perform the operation and a joystick mechanism 52. The joystick mechanism 52 is provided with a main body 54 fixed to the second operation unit 41 and a lever 53 tiltable relative to the main body 54. The rotation input portion 51 is fixed to the upper end of the lever 53.

Figure 5:
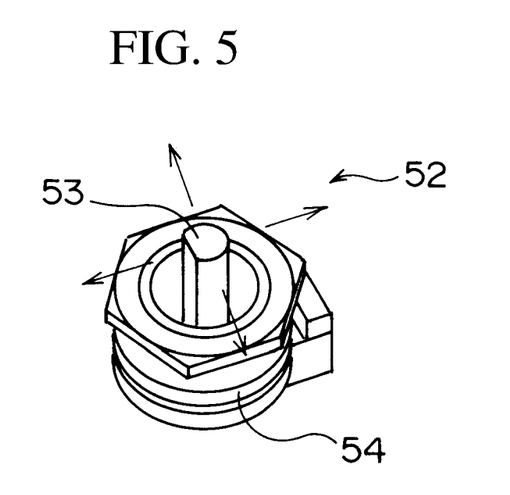
FIG. 5 is a perspective view showing a function of a joystick mechanism 52.
Figure 6:
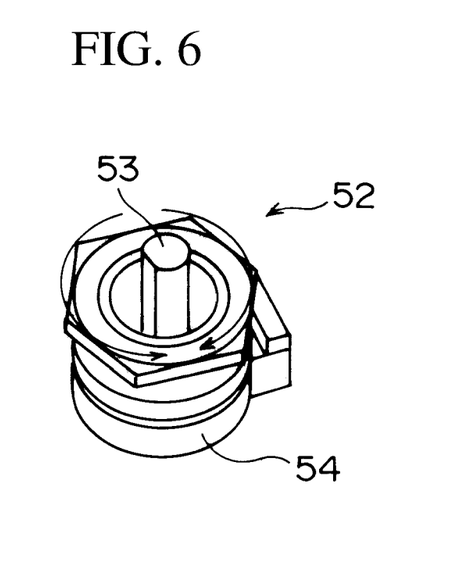
FIG. 6 is a perspective view showing a function of a joystick mechanism 52.
Figure 7:
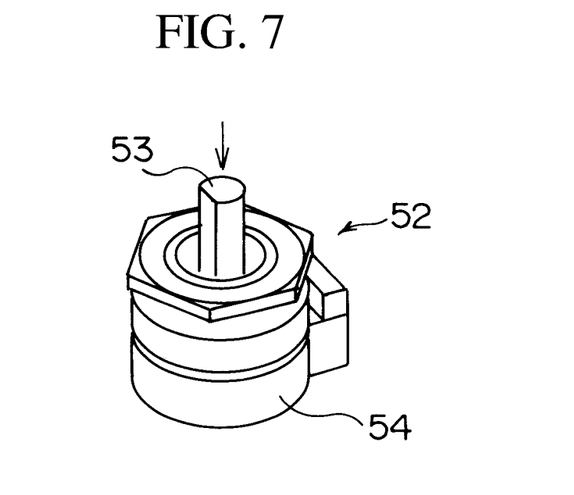
FIG. 7 is a perspective view showing a function of a joystick mechanism 52.

FIG. 5 to FIG. 7 are perspective views showing functions of the joystick mechanism 52 constituting the operation unit 50.

This joystick mechanism 52 is a multifunctional device with functions of a joystick, a rotary encoder, and a push switch. In this joystick mechanism 52, as shown by the arrows in FIG. 5, the lever 53 can be tilted in four directions with respect to the main body 54, and functions as a joystick to transmit a signal in the tilted direction. In the joystick mechanism 52, the lever 53 is rotatable with respect to the main body 54 as shown by the arrows in FIG. 6, which functions as a rotary encoder to transmit a signal about the rotation direction and the rotation angle. Note that the lever 53 has a dial-type configuration in which the rotation is regulated at regular rotation angle intervals. Further, in this joystick mechanism 52, as shown by the arrow in FIG. 7, the lever 53 can be pushed in in the axial direction of the lever 53 with respect to the main body 54, and functions as a push switch to transmit a signal according to the push-in operation.

Figure 8:
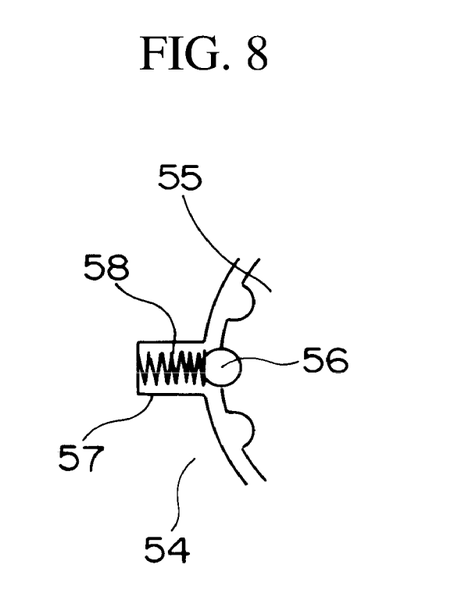
FIG. 8 is a schematic diagram of a rotation regulation mechanism for regulating the rotation of a lever 53 of a joystick mechanism 52 at every predetermined rotation angle.

FIG. 8 is a schematic diagram of a rotation regulation mechanism for regulating the rotation of the lever 53 of the joystick mechanism 52 at every predetermined rotation angle.

The lever 53 of the joystick mechanism 52 is connected to a disk 55 whose outer periphery is notched at a constant pitch. On the other hand, a spring 58 is disposed in a recess 57 formed on the main body 54 of the joystick mechanism 52, and a ball 56 is disposed on the front end of the spring 58. When an operator rotates the lever 53 via the rotation input portion 51 shown in FIG. 4, after the ball 56 is detached from the notch formed in the disk 55, it engages with the adjacent notch again, thereby regulating the rotation of the lever 53 at regular rotation angle intervals. The rotation regulation mechanism for the lever 53 of the joystick mechanism 52 shown in FIG. 8 is one example, and the rotation regulation may be performed by another mechanical structure.

In the operation unit 50 having the above-described configuration, an operator can perform the tilting operation, the rotating operation, and the push-in operation of the lever 53 of the joystick mechanism 52 via the rotation input portion 51. The joystick mechanism 52 used for this operation unit 50 is commercially available as an industrial component.

Figure 9:
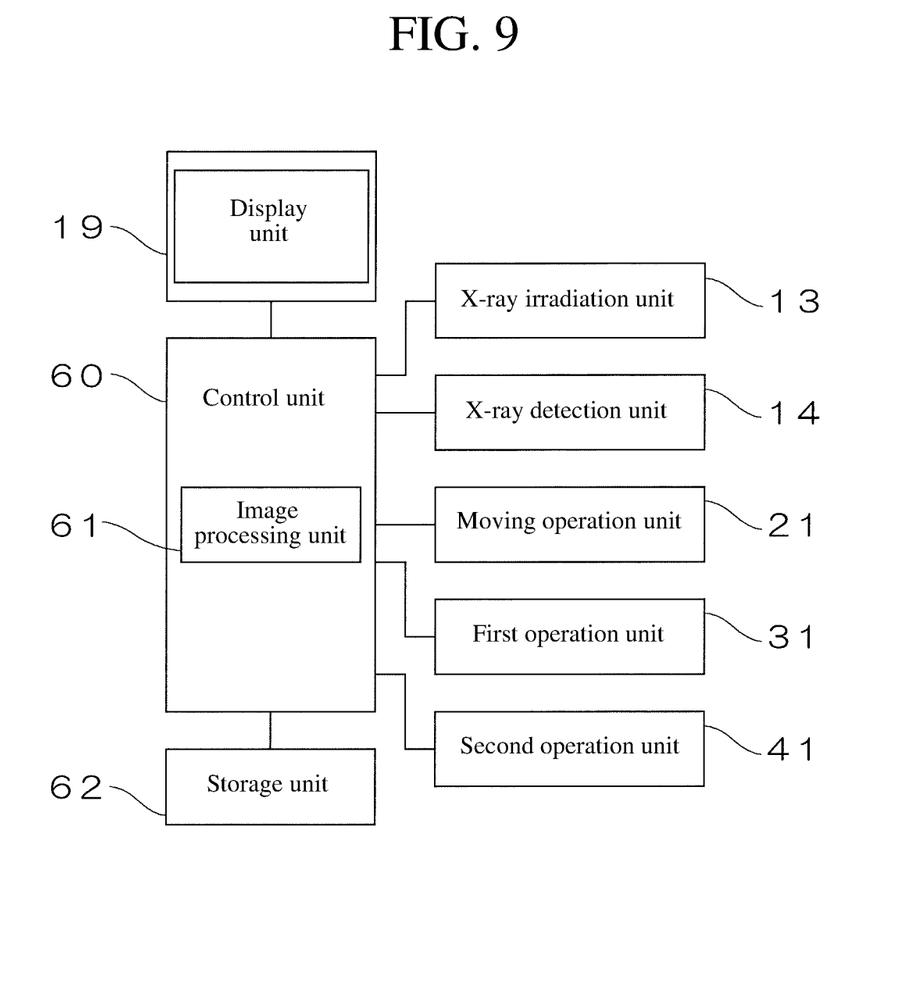
FIG. 9 shows a block diagram showing a main control system of an X-ray imaging apparatus.

FIG. 9 shows a block diagram showing a main control system of the X-ray imaging apparatus.

This X-ray imaging apparatus is provided with a control unit 60 for controlling the entire apparatus. This control unit 60 is composed of a computer in which software is installed. The function of each part included in this control unit 60 is realized by executing the software installed in the computer. The control unit 60 is connected to the display unit 19, the X-ray irradiation unit 13, the X-ray detection unit 14, the moving operation unit 21, the first operation unit 31, and the second operation unit 41 described above.

Further, the X-ray imaging apparatus includes a storage unit 62 composed of a hard disk or the like. Images continuously captured at a predetermined frame rate by the imaging system composed of the X-ray irradiation unit 13 and the X-ray detection unit 14 are stored in this storage unit 62 as a moving image. In this storage unit 62, a plurality of moving images that have been continuously captured now or in the past are stored.

Figure 10:
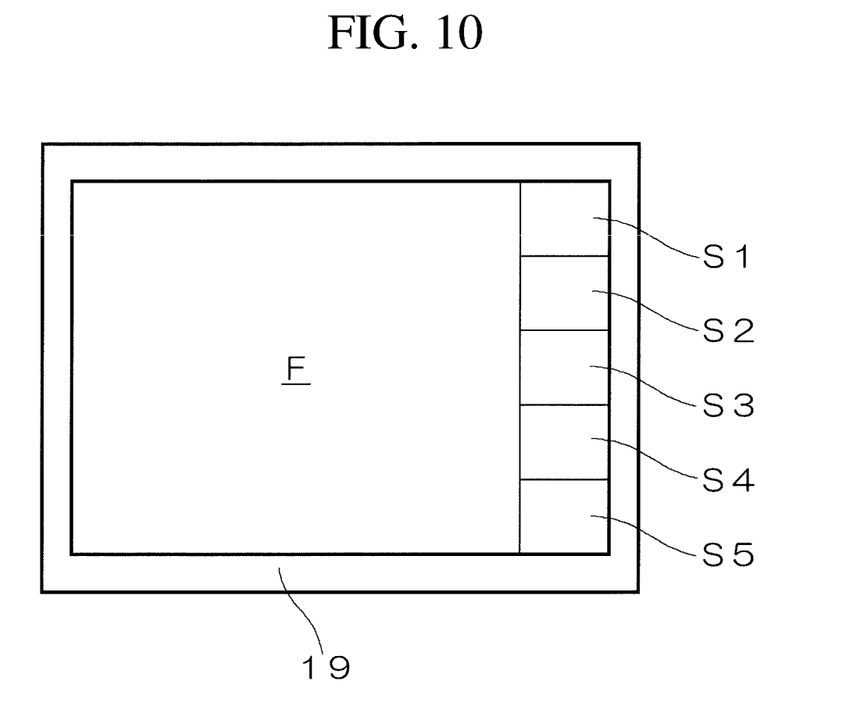
FIG. 10 is a schematic diagram showing one embodiment in which a moving image is displayed on a display unit 19.

FIG. 10 is a schematic diagram illustrating one embodiment of displaying a moving image on the display unit 19.

Five types of moving images selected from a plurality of moving images captured by the imaging system composed of the X-ray irradiation unit 13 and the X-ray detection unit 14 and stored in the storage unit 62 are displayed as thumbnails S1 to S5 in the display unit 19. Then, a moving image selected from them is displayed on the display region F for a moving image at a predetermined frame rate.

Next, in the X-ray imaging apparatus having the above-described configuration, an operation of switching moving images to be displayed on the display unit 19 by operating the operation unit 50 in the second operation unit 41 will be described. Note that the display of the moving image by operating the operation unit 50 described below is performed by receiving an operation signal from the second operation unit 41 by the image processing unit 61 in the control unit 60.

When an operator operates the rotation input portion 51 of the operation unit 50 to tilt the lever 53 of the joystick mechanism 52 in the up-down direction in a state in which the moving image thumbnails S1 to S5 are displayed on the display unit 19 in the manner shown in FIG. 10, a selection operation of the thumbnails S1 to S5 is performed. When the operator operates the rotation input portion 51 to tilt the lever 53 of the joystick mechanism 52 in the up-down direction to select of any of the thumbnails S1 to S5 and the corresponding moving image is displayed on the display region F, and pushed in the lever 53 by operating the rotation input portion 51, the playback of the moving image displayed on the display region F is started. The playback is temporarily stopped when the lever 53 is pushed in again, and the moving image is displayed in the display region F as a still image.

In this state, when the operator rotates the lever 53 of the joystick mechanism 52 by operating the rotation input portion 51, a frame feeding operation (so-called "frame-by-frame playback") operation in which the frame of the moving image displayed on the display region F is sequentially fed is performed. At this time, the rotation input portion 51 and the lever 53 have a dial-type configuration in which the rotation is restricted at regular rotation angle intervals, and the image processing unit 61 executes the frame feeding operation in which the frame of the moving image to be displayed on the display unit 19 is changed by one frame every time the rotation input portion 51 and the lever 53 rotate by a constant rotation angle.

Further, in a state in which a moving image is displayed in the display region F, when the operator tilts the lever 53 of the joystick mechanism 52 in the left-right direction by operating the rotation input portion 51 of the operation unit 50, the playback speed of the moving image displayed in the display region F is changed. More specifically, when the lever 53 is tilted, the moving image is subjected to the fast-forward playback in a direction corresponding to the tilting direction of the lever 53. The fast-forward playback speed at this time may be constant or may be changed in proportion to the tilt angle of the lever 53. When the lever 53 is returned to the neutral position, the moving image fast-forward playback is stopped.

When the tilting operation of the lever 53 and the rotating operation of the rotation input portion 51 are performed simultaneously by the operator, the image processing unit 61 preferentially performs the frame feeding operation corresponding to the operation of the rotation input portion 51. This prevents the moving image from being fast-forwarded during the frame feeding operation.

The rotating and tilting operation of the rotation input portion 51 by the operator can be performed blindly without looking at the rotation input portion 51 as long as the operator grips the rotation input portion 51. Therefore, even in a case where the operation unit 50 is covered by a sterilization cover, it is possible to accurately perform the tilting operation of the lever 53 and the rotating operation of the rotation input portion 51, so that it is possible to easily and appropriately perform the selection operation or the playback operation of the moving image and the frame feeding operation.

It will be appreciated by those skilled in the art that the above-described exemplary embodiments are illustrative of the following aspects.

(Item 1)

A radiographic imaging apparatus comprising:

an imaging system configured to perform continuous imaging at a predetermined frame rate by detecting radiation by a radiation detection unit 14, the radiation being emitted from a radiation irradiation unit 13 and passed through a subject;

a storage unit 62 configured to store a plurality of radiographic images continuously captured by the imaging system as a moving image;

a display unit 19;

an operation unit 50 configured to perform an operation of a display of the moving image for the display unit 19, the moving image being stored in the storage unit 62$t$; and an image processing unit 61 configured to cause the display unit 19 to display the moving image stored in the storage unit 62 according to an operation of the operation unit, wherein the operation unit 50 includes a tiltable lever 53 and a rotation input portion 51 provided at an upper end of the lever 53, and wherein the image processing unit performs a selection or a playback of the moving image to be displayed on the display unit according to a tilting operation of the lever, and performs a frame feeding operation of the moving image to be displayed on the display unit according to a rotating operation of the rotation input portion.

According to the radiographic imaging apparatus as recited in the above-described Item 1, even in a case where the operation unit is covered with a sterilization cover, the tilting operation of the lever and the rotating operation of the rotation input portion can be accurately performed, so that the selecting operation and the playback operation of the moving image and the frame feeding operation can be easily and properly performed.

(Item 2)

The radiographic imaging apparatus as recited in the above-described Item 1, wherein the rotation input portion 51 has a dial-type configuration in which a rotation is regulated at predetermined rotation angle intervals, and wherein the image processing unit 61 changes a frame of the moving image to be displayed on the display unit 19 by one frame each time the rotation input portion 51 is rotated by a predetermined rotation angle.

According to the radiographic imaging apparatus as recited in the above-described Item 2, the frame feeding operation of changing the frame of the moving image only by one frame can be executed accurately and easily.
(Item 3)

The radiographic imaging apparatus as recited in the above-described Item 1 or 2, wherein the lever 53 is capable of being pushed in in an axial direction, and wherein the image processing unit 61 performs a selection operation of the moving image and a change operation of a playback speed according to the tilting operation of the lever 53, and performs a playback operation and a stop operation of the moving image according to a push-in operation of the lever 53.

According to the radiographic imaging apparatus as recited in the above-described Item 3, it is possible to perform the moving image selection operation, the playback speed change operation, and the playback and stop operation of the moving image.
(Item 4)

The radiographic imaging apparatus as recited in any one of the above-described Items 1 to 3, wherein the image processing unit 61 preferentially performs processing corresponding to an operation of the rotation input portion when an operation of the lever 53 and an operation of the rotation input portion 51 are performed simultaneously.

According to the radiographic imaging apparatus as recited in the above-described Item 4, it is possible to prevent the selection or the playback of the moving image from being erroneously executed while the frame feeding operation is being executed.

It should be noted that the foregoing description is for the purpose of explaining embodiments of the present invention and is not intended to limit the present invention.

DESCRIPTION OF SYMBOLS

13: X-ray irradiation unit
14: X-ray detection unit
15: C-shaped arm
16: Top board
17: Support portion
19: Display unit
20: Rail
21: Moving operation unit
31: First operation unit
32: Touch panel
41: Second operation unit
50: Operation unit
51: Rotation input portion
52: Joystick mechanism
53: Lever
54: Main body
55: Disk
56: Ball
58: Spring
60: Control unit
61: Image processing unit
62: Storage unit

The invention claimed is:

1. A radiographic imaging apparatus comprising:
an imaging system configured to perform continuous imaging at a predetermined frame rate by detecting radiation by a radiation detection unit, the radiation being emitted from a radiation irradiation unit and passed through a subject;
a storage unit configured to store a plurality of radiographic images continuously captured by the imaging system as a moving image;
a display unit;
an operation unit configured to perform an operation of a display of the moving image for the display unit, the moving image being stored in the storage unit; and
an image processing unit configured to cause the display unit to display the moving image stored in the storage unit according to an operation of the operation unit,
wherein the operation unit includes a tiltable lever and a rotation input portion provided at an upper end of the lever, and
wherein the image processing unit performs a selection or a playback of the moving image to be displayed on the display unit according to a tilting operation of the lever, and performs a frame feeding operation of the moving image to be displayed on the display unit according to a rotating operation of the rotation input portion.

2. The radiographic imaging apparatus as recited in claim 1,
wherein the rotation input portion has a dial-type configuration in which a rotation is regulated at predetermined rotation angle intervals, and
wherein the image processing unit changes a frame of the moving image to be displayed on the display unit by one frame each time the rotation input portion is rotated by a predetermined rotation angle.

3. The radiographic imaging apparatus as recited in claim 1,
wherein the lever is capable of being pushed in in an axial direction, and
wherein the image processing unit performs a selection operation of the moving image and a change operation of a playback speed according to the tilting operation of the lever, and performs a playback operation and a stop operation of the moving image according to a push-in operation of the lever.

4. The radiographic imaging apparatus as recited in claim 1,
wherein the image processing unit preferentially performs processing corresponding to an operation of the rotation input portion when an operation of the lever and an operation of the rotation input portion are performed simultaneously.

* * * * *